US006984722B2

(12) United States Patent
Christopher et al.

(10) Patent No.: US 6,984,722 B2
(45) Date of Patent: Jan. 10, 2006

(54) CATIONIC GROUP 3 CATALYST SYSTEM

(75) Inventors: Joseph N Christopher, League City, TX (US); Kevin R. Squire, Kingwood, TX (US); Jo Ann M. Canich, Houston, TX (US); Timothy D. Shaffer, Houston, TX (US)

(73) Assignee: ExxonMobil Chemical Patents Inc., Houston, TX (US)

( * ) Notice: Subject to any disclaimer, the term of this patent is extended or adjusted under 35 U.S.C. 154(b) by 580 days.

(21) Appl. No.: 09/997,777

(22) Filed: Nov. 29, 2001

(65) Prior Publication Data

US 2002/0065191 A1 May 30, 2002

Related U.S. Application Data

(62) Division of application No. 09/408,050, filed on Sep. 29, 1999, now Pat. No. 6,403,773.
(60) Provisional application No. 60/102,420, filed on Sep. 30, 1998.

(51) Int. Cl.
*C07F 5/00* (2006.01)
*C08F 4/44* (2006.01)

(52) U.S. Cl. .................. 534/15; 502/100; 502/150; 502/152; 526/160; 526/161; 526/171; 526/172

(58) Field of Classification Search ............... 534/15; 502/100, 150, 152, 155; 526/160, 161, 171, 526/172
See application file for complete search history.

(56) References Cited

U.S. PATENT DOCUMENTS

| 4,543,399 A | 9/1985 | Jenkins et al. ............ 526/70 |
| 4,588,790 A | 5/1986 | Jenkins et al. ............ 526/70 |
| 4,665,208 A | 5/1987 | Welborn, Jr. et al. ....... 556/179 |
| 4,874,734 A | 10/1989 | Kioka et al. ............... 502/104 |

(Continued)

FOREIGN PATENT DOCUMENTS

| EP | 0 279 586 | 8/1988 |
| EP | 0 426 637 | 5/1991 |
| EP | 0 427 697 | 5/1991 |
| EP | 0 495 375 | 7/1992 |
| EP | 0 516 476 | 12/1992 |
| EP | 0 520 732 | 12/1992 |
| EP | 0 561 476 | 9/1993 |
| EP | 0 573 403 | 12/1993 |
| EP | 0 594 218 | 4/1994 |
| EP | 0 765 888 | 4/1997 |
| WO | WO 91/09882 | 7/1991 |
| WO | WO 92/00333 | 1/1992 |
| WO | WO 93/11172 | 6/1993 |
| WO | WO 93/14132 | 7/1993 |
| WO | WO 94/03506 | 2/1994 |
| WO | WO 94/07928 | 4/1994 |
| WO | WO 94/10180 | 5/1994 |
| WO | WO 95/07941 | 3/1995 |
| WO | WO 95/07942 | 3/1995 |
| WO | WO 96/04319 | 2/1996 |
| WO | WO 96/13529 | 5/1996 |
| WO | WO 96/23010 | 8/1996 |
| WO | WO 97/23493 | 7/1997 |
| WO | WO 97/42228 | 11/1997 |
| WO | WO 97/42241 | 11/1997 |
| WO | WO 98/22486 | 5/1998 |

OTHER PUBLICATIONS

α"Agostic" Assistance in Ziegler–Natta Polymerization of Olefins. Deuterium Isotopic Perturbation of Sterochemistry Indicating Coordination of an α C–H Bond in Chain Propagation, Piers, et al, J. Am. Chem. Soc., vol. 112, pp. 9406–9407 (1990).

"[{($\eta^5$–$C_5Me_4$)$Me_2Si${$\eta^1$–$NCMe_3$}{($PMe_3$)ScH]$_2$: A Unique Example of a Single–Component α–Olefin Polymerization Catalyst", Shapiro, et al, Organometallics, vol. 9, pp. 867–869, (1990).

"Iso–Specific Ziegler–Natta Polymerization of α–Olefins with a single–Component Organoyttrium Catalyst", Coughlin, et al, J. Am. Chem. Soc., vol. 114, pp. 7606–7607, (1992).

"Model Ziegler–Natta α–Olefin Polymerization Catalysts Derived fron [{($\eta^5$–$C_5Me_4$)$SiMe_2(\eta^1$–$NCMe_3$)}($PMe_3$)Sc($\mu_2$–H)]$_2$ Synthesis, Structures, and Kinetic and Equilibrium Investigations of the Catalytically Active Species in Solution", Shapiro, et al. J. Am. Chem. Soc., vol. 116, pp. 4423–4640, (1994.

"Competitive Chain Transfer by β–Hydrogen and β–Methyl Elimination for the Model Ziegler–Natta Olefin Polymerization System [$Me_2Si(\eta^5$–$C_5Me_4$)2] Sc{$CH_2CH(CH_3)$}($PMe_3$)", Hajela, et al, Organometallics, vol. 13, pp. 1147–1154, (1994).

"Polymerization of αOlefins by Chelating Diamide Complexes of Titanium", Scollard, et al, Macromolecules, vol. 29, pp. 5241–5243, (1996).

"Synthesis and Characterization of the Five–Coordinate Scandium Dialkyl Complexes Sc$R_2$[N(Si$Me_2CH_2PPr^1_2$)$_2$] (R=Me, Et, $CH_2SiMe_3$)", Fryzuk et al., Organometallics vol. 15, (1996) pp 3329–3336.

"Synthesis of Dialkylscandium Complexes Supported by β–Diketiminato Ligands and Activation with Tris (pentafluorophenyl) borane", Lee et al., Organometallics, vol. 18., 2947 (1999).

(Continued)

Primary Examiner—Robert D. Harlan

(57) ABSTRACT

A cationic Group 3 or Lanthanide metal complex for coordination polymerization of olefins is disclosed. The precursor metal complex is stabilized by a monoanionic bidentate ancillary ligand and two monoanionic ligands. The ancillary ligand and the transition metal form a metallocycle having at least five primary atoms, counting any π-bound cyclopentadienyl group in the metallocycle as two primary atoms. Olefin polymerization is exemplified.

13 Claims, No Drawings

U.S. PATENT DOCUMENTS

| | | | |
|---|---|---|---|
| 4,908,463 A | 3/1990 | Bottelberghe | 556/179 |
| 4,924,018 A | 5/1990 | Bottelberghe | 556/179 |
| 4,952,540 A | 8/1990 | Kioka et al. | 502/9 |
| 4,968,827 A | 11/1990 | Davis | 556/179 |
| 5,001,205 A | 3/1991 | Hoel | 526/128 |
| 5,028,670 A | 7/1991 | Chinh et al. | 526/73 |
| 5,041,584 A | 8/1991 | Crapo et al. | 556/179 |
| 5,057,475 A | 10/1991 | Canich et al. | 502/104 |
| 5,064,802 A | 11/1991 | Stevens et al. | 502/155 |
| 5,091,352 A | 2/1992 | Kioka et al. | 502/103 |
| 5,103,031 A | 4/1992 | Smith, Jr. | 556/179 |
| 5,132,380 A | 7/1992 | Stevens et al. | 526/125 |
| 5,153,157 A | 10/1992 | Hlatky et al. | 502/117 |
| 5,157,137 A | 10/1992 | Sangokoya | 556/179 |
| 5,198,401 A | 3/1993 | Turner et al. | 502/155 |
| 5,204,419 A | 4/1993 | Tsutsui et al. | 526/153 |
| 5,206,199 A | 4/1993 | Kioka et al. | 502/117 |
| 5,227,440 A | 7/1993 | Canich et al. | 526/129 |
| 5,229,478 A | 7/1993 | Floyd et al. | 526/160 |
| 5,235,081 A | 8/1993 | Sangokoya | 556/179 |
| 5,241,025 A | 8/1993 | Hlatky et al. | 526/129 |
| 5,248,801 A | 9/1993 | Sangokoya | 556/179 |
| 5,278,119 A | 1/1994 | Turner et al. | 502/155 |
| 5,312,881 A | 5/1994 | Marks et al. | 526/126 |
| 5,318,935 A | 6/1994 | Canich et al. | 502/117 |
| 5,321,106 A | 6/1994 | LaPointe | 526/126 |
| 5,329,032 A | 7/1994 | Tran et al. | 556/179 |
| 5,347,024 A | 9/1994 | Nickias et al. | 556/11 |
| 5,352,749 A | 10/1994 | DeChellis et al. | 526/68 |
| 5,382,638 A | 1/1995 | Bontemps et al. | 526/67 |
| 5,387,568 A | 2/1995 | Ewen et al. | 502/104 |
| 5,405,922 A | 4/1995 | DeChellis et al. | 526/68 |
| 5,408,017 A | 4/1995 | Turner et al. | 526/134 |
| 5,422,325 A | 6/1995 | Jejelowo et al. | 502/104 |
| 5,427,991 A | 6/1995 | Turner | 502/103 |
| 5,436,304 A | 7/1995 | Griffin et al. | 526/68 |
| 5,453,471 A | 9/1995 | Bernier et al. | 526/68 |
| 5,455,317 A | 10/1995 | Marks et al. | 526/126 |
| 5,462,999 A | 10/1995 | Griffin et al. | 526/68 |
| 5,463,999 A | 11/1995 | Taruya et al. | 123/647 |
| 5,464,906 A | 11/1995 | Patton et al. | 525/240 |
| 5,466,649 A | 11/1995 | Jejelowo | 502/120 |
| 5,486,632 A | 1/1996 | Devore et al. | 556/11 |
| 5,498,582 A | 3/1996 | Krause et al. | 502/103 |
| 5,527,929 A | 6/1996 | Timmers et al. | 556/7 |
| 5,563,219 A | 10/1996 | Yasuda et al. | 525/269 |
| 5,599,671 A | 2/1997 | Jacobson et al. | 435/6 |
| 5,624,878 A | 4/1997 | Devore et al. | 502/152 |
| 5,643,847 A | 7/1997 | Walzer, Jr. | 502/117 |
| 5,707,913 A | 1/1998 | Schlund et al. | 502/102 |
| 6,403,773 B1 * | 6/2002 | Christopher et al. | 534/15 |
| 6,677,441 B2 * | 1/2004 | Christopher et al. | 534/15 |

OTHER PUBLICATIONS

"On the Synthesis of monopentamethylcyclopentadienyl derivatives of yttrium, lanthanum, and cerium", Booji et al., Journal of Organometallic Chemistry, 364 (1989) pp 79–86.

"(Aminotroponiminato)yttrium Amides as Catalyst in Alkyne Hydroamination", Burgstein et al., *Organometallics, vol. 17, pp. 1452–1454* (1998).

"Synthesis of Dialkylscandium Complexes Supported by B–Diketiminato Ligands and Activation with Tris(pentafluorophenyl)borane", Lee et al., *Organomtallics*, vol. 18, pp. 2947–2949, (1999).

"Organometallic Compounds of the lanthanides. CXXI. Donor–substituted lanthanidocenes. Synthesis of mixed unbridged lanthanidocene chloride and alkyl derivatives" Schumann et al., *Journal of Organometallic Chemistry*. vol. 562, pp. 255–262 (1998).

"Single site Polymerization of ethylene and I–olefins initiated by rare earth metal complexes", Ihara et al., *Macromol. Chem. Phys.*, vol. 197, pp. 1909–1917 (1996).

* cited by examiner

CATIONIC GROUP 3 CATALYST SYSTEM

RELATED APPLICATIONS

This application is a Divisional of U.S. application Ser. No. 09/408,050, now U.S. Pat. No. 6,403,773 filed on Sep. 29, 1999. application Ser. No. 09/408,050 claims priority from U.S. Provisional Application Ser. No. 60/102,420, filed Sep. 30, 1998.

FIELD OF THE INVENTION

This invention relates to certain transition metal compounds from Group 3 of the Periodic Table of Elements, and to a catalyst system comprising a Group 3 or Lanthanide transition metal compound and alumoxane, modified alumoxane, non-coordinating anion activator, Lewis acid, or the like to form an active cationic catalyst species for the production of polyolefins such as polyethylene, polypropylene and alpha-olefin copolymers of ethylene and propylene having a high molecular weight.

BACKGROUND OF THE INVENTION

Neutral scandium compounds having two univalent ancillary ligands or a bidentate, divalent ancillary ligand are known from Shapiro et al., *Organometallics*, vol. 9, pp. 867–869 (1990); Piers et al., *J. Am. Chem Soc.*, vol. 112, pp. 9406–9407 (1990); Shapiro et al., *J. Am. Chem Soc.*, vol. 116, pp. 4623–4640 (1994); Hajela et al., *Organometallics*, vol. 13, pp. 1147–1154 (1994); and U.S. Pat. No. 5,563,219 to Yasuda et al. Similar yttrium, lanthanum and cerium complexes are disclosed in Booij et al., *Journal of Organometallic Chemistry*, vol. 364, pp. 79–86 (1989) and Coughlin et al., *J. Am. Chem. Soc.*, vol. 114, pp. 7606–7607 (1992). Similar polymerizations with a metal scandium complex having a bidentate, divalent ancillary ligand using a non-ionizing cocatalyst is known from U.S. Pat. No. 5,464,906 to Patton et. al.

Group 3–10 metallocyclic catalyst complexes are described in U.S. Pat. Nos. 5,312,881 and 5,455,317, both to Marks et al.; U.S. Pat. No. 5,064,802 to Stevens et al.; and EP 0765 888A2.

Polymerization of olefins with cationic Group 4 metal complexes is illustrated in WO 96/13529 and WO 97/42228. Boratabenzene complexes of Group 3–5 metals are disclosed in WO 97/23493.

Amidinato complexes of Group 3–6 metals are disclosed in U.S. Pat. No. 5,707,913 to Schlund et al. Group 4 bisamido catalysts are disclosed in U.S. Pat. No. 5,318,935 to Canich, et al., and related bidentate bisarylamido catalysts are disclosed by D. H. McConville, et al, *Macromolecules* 1996, 29, 5241–5243.

SUMMARY OF THE INVENTION

The present invention is directed to a catalyst system for coordination polymerization comprising a cationic Group 3 or Lanthanide metal stabilized by a monoanionic bidentate ancillary ligand and two monoanionic ligands. The ancillary ligand, together with the metal, forms a metallocycle comprising a ring of at least five primary atoms, counting any $\eta^5$-bonded cyclopentadienyl in the metallocycle as two primary metallocycle atoms. The metal is preferably scandium, yttrium or lanthanum.

In one embodiment, the monoanionic bidentate ancillary ligand, A, has the formula $(C_5H_{4-x}R_x)TE$ wherein x is a number from 0 to 4 denoting the degree of substitution; each R is, independently, a radical selected from $C_1$–$C_{20}$ hydrocarbyl radicals, $C_1$–$C_{20}$ substituted hydrocarbyl radicals wherein one or more hydrogen atoms are replaced by a halogen atom, amido, phosphido, alkoxy or aryloxy or any other radical containing a Lewis acidic or basic functionality, $C_1$–$C_{20}$ hydrocarbyl-substituted metalloid radicals wherein the metalloid is selected from Group 14 of the Periodic Table of the Elements, and halogen radicals, or $C_5H_{4-x}R_x$ is a cyclopentadienyl ring in which two adjacent R-groups are joined to form a $C_4$–$C_{20}$ ring to give a saturated or unsaturated polycyclic cyclopentadienyl ligand which may additionally be substituted with R groups, and may contain a heteroatom within the ring; T is a covalent bridging group containing a Group 14 or 15 element; and E is a π donating hydrocarbyl, π donating heterohydrocarbyl, or other π-donating ligand covalently bound to T such as, for example, allyl, phenyl, benzyl, pyridyl or the like, or E is $JR'_z$ wherein J is an element from Group 15 or 16, z is 2 when J is a Group 15 element and 1 when J is a Group 16 element, each R' is independently a radical selected from $C_1$–$C_{20}$ hydrocarbyl radicals, substituted $C_1$–$C_{20}$ hydrocarbyl radicals wherein one or more hydrogen atoms is replaced by a halogen atom, and $C_1$–$C_{20}$ hydrocarbyl-substituted metalloid radicals wherein the metalloid is selected from Group 14 of the Periodic Table of the Elements.

Heterocyclic pi donating ligands wherein one to three ring carbons of the $C_5H_{4-x}R_x$ ligand is replaced by a Group 15 or 16 heteroatom; substituted or unsubstituted boratabenzene ligands; substituted or unsubstituted allyl ligands; substituted or unsubstituted pentadienyl ligands; or other delocalized pi-bonded ligands may also be used in place of the $C_5H_{4-x}R_x$ ligand.

In another embodiment, as represented by structure (I), the monoanionic bidentate ancillary ligand, A, has the formula —NR'=T'-NR'— wherein N is nitrogen and T' is a covalent bridging group selected from =C(R)—[C(R)=C(R)]$_n$— and

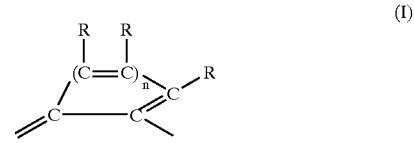

(I)

wherein each R' is independently as defined above, each R is independently as defined above, except that R independently may also be hydrogen except for R groups attached to the carbon atoms directly bonded to the nitrogen atoms.

In a further embodiment, a typical polymerization process according to the present invention, such as the polymerization or copolymerization of olefins, comprises the steps of activating the transition metal component to a cationic form and contacting ethylene or $C_3$–$C_{20}$ alpha-olefins alone or with other unsaturated monomers including $C_3$–$C_{20}$ alpha-olefins, $C_5$–$C_{20}$ diolefins, and/or acetylenically unsaturated monomers, either alone or in combination with other olefins and/or other unsaturated monomers, with a catalyst comprising, in a suitable polymerization diluent, the activated cationic transition metal component of the invention. The catalyst is activated with an alumoxane, modified alumoxane, non-coordinating anion activator, Lewis acid or the like, or combinations, in an amount to provide a molar ratio of aluminum, non-coordinating anion, or Lewis acid to transition metal of from about 1:10 to about 20,000:1 or more; and reacts with the monomer(s) at a temperature from about −100° C. to about 300° C. for a time from about one second to about 10 hours to produce a polyolefin having a weight average molecular weight of from about 1000 or less to about 5,000,000 or more and a molecular weight distribution of from about 1.5 to about 15.0 or greater.

DETAILED DESCRIPTION OF THE INVENTION

The Group 3 transition metal component of the catalyst system of the invention can be defined broadly by the formula:

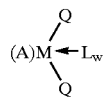
(II)

wherein M is a Group 3 or Lanthanide metal;

A is a monoanionic, bidentate ancillary ligand which forms a metallocycle with M comprising at least 5 primary atoms, provided that any cyclopentadienyl group or other delocalized pi-bonded ligand in the metallocycle is counted as two primary metallocycle atoms; each Q is independently a monoanionic ligand such as a radical selected from halide, hydride, substituted or unsubstituted $C_1$–$C_{20}$ hydrocarbyl, hydrocarbylsilyl, alkoxide, aryloxide, amide or phosphide or both Q together may be an alkylidene or a cyclometallated hydrocarbyl or any other divalent anionic chelating ligand, or a diene, with the proviso that where any Q is a hydrocarbyl radical, such Q is not a substituted or unsubstituted cyclopentadienyl radical;

L is a neutral Lewis base such as, for example, diethyl ether, tetrahydrofuran, dimethylaniline, trimethylphosphine, lithium chloride or the like, and can also be optionally covalently bound to one or both Q, provided Q is not hydride or halide. L can also be a second transition metal of the same type, i.e. the transition metal component can be dimeric; and w is a number from 0 to 3.

In cationic form as activated for olefin polymerization, the transition metal complex has the formula:

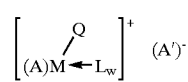
(III)

wherein M, A, Q, L and w are as defined above and A' is a weakly or noncoordinating anion which counterbalances the cationic complex.

In a preferred embodiment, the transition metal component of the catalyst system has the formula:

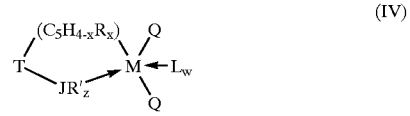
(IV)

wherein $C_5H_{4-x}R_x$ is typically a cyclopentadienyl ring covalently π-bound to M and substituted with from zero to four substituent groups R, x is a number from 0 to 4 denoting the degree of substitution, and each R is, independently, a radical selected from $C_1$–$C_{20}$ hydrocarbyl radicals, $C_1$–$C_{20}$ substituted hydrocarbyl radicals wherein one or more hydrogen atoms are replaced by a halogen atom, amido, phosphido, alkoxy or aryloxy or any other radical containing a Lewis acidic or basic functionality, $C_1$–$C_{20}$ hydrocarbyl-substituted metalloid radicals wherein the metalloid is selected from Group 14 of the Periodic Table of the Elements, and halogen radicals, or $C_5H_{4-x}R_x$ is a cyclopentadienyl ring in which two adjacent R-groups are joined to form a $C_4$–$C_{20}$ ring to give a saturated or unsaturated polycyclic cyclopentadienyl ligand which may additionally be substituted with R groups, and may contain a heteroatom within the ring; $C_5H_{4-x}R_x$ may alternatively be replaced with a heteroatom-containing 5-membered monovalent anionic ring group covalently π-bound to M, said heteroatoms being selected from the non-carbon Group 13–15 atoms, preferably boron, silicon, germanium, nitrogen or phosphorus. Most typically one heteroatom will replace one of the carbon atoms in the 5-member ring. Additionally, two or more adjacent R groups may be joined to form a 4 to 20 atom ring forming a saturated or unsaturated polycyclic cyclopentadienyl ligand which may additionally contain a non-carbon group 14–16 heteroatom within the ring. Such ligands are described in WO 98/22486 which is referred to for information and incorporated by reference for purposes of US patent practice.

T is a covalent bridging group containing a Group 14 or 15 element such as, but not limited to, a dialkyl, alkylaryl or diaryl silicon or germanium radical, alkyl or aryl phosphine or amine radical, or a hydrocarbyl radical such as methylene, ethylene, isopropylene or the like.

J is a Group 15 or 16 element; z is 2 when J is a Group 15 element and 1 when J is a Group 16 element; each R' is independently a radical selected from $C_1$–$C_{20}$ hydrocarbyl radicals and substituted $C_1$–$C_{20}$ hydrocarbyl radicals wherein one or more hydrogen atoms is replaced by a halogen atom, amido, phosphido, alkoxy, aryloxy, metalloid or any other radical containing a Lewis acidic or basic functionality, and $C_1$–$C_{20}$ hydrocarbyl-substituted metalloid radicals wherein the metalloid is selected from Group 14 of the Periodic Table of the Elements.

Q, L and w are defined above.

Exemplary hydrocarbyl radicals for Q in all of the above formulae are methyl, ethyl, propyl, butyl, amyl, isoamyl, hexyl, isobutyl, heptyl, octyl, nonyl, decyl, cetyl, 2-ethylhexyl, phenyl, benzyl and the like, with benzyl being preferred. Exemplary halogen atoms for Q include chlorine, bromine, fluorine and iodine, with chlorine being preferred. Exemplary alkoxides and aryloxides for Q are methoxide, phenoxide and substituted phenoxides such as 4-methylphenoxide. Exemplary amides for Q are dimethylamide, diethylamide, methylethylamide, di-t-butylamide, diisopropylamide and the like. Exemplary arylamides are diphenylamide and any other substituted phenylamides. Exemplary phosphides for Q are diphenylphosphide, dicyclohexylphosphide, diethylphosphide, dimethylphosphide and the like. Exemplary alkylidene radicals for both Q together are methylidene, ethylidene and propylidene. Exemplary cyclometallated hydrocarbyl radicals for both Q together are propylene, and isomers of butylene, pentylene, hexylene and octylene. Exemplary dienes for both Q together are 1,3-butadiene, 1,3-pentadiene, 1,4-pentadiene, 1,3-hexadiene, 1,4-hexadiene, 1,5-hexadiene, 2,4-dimethyl-1,3-butadiene, 2-methyl-1,3-pentadiene, 2-methyl-1,3-hexadiene and 2,4-hexaidiene.

Suitable hydrocarbyl radicals, for R or R' in all the above formulae, will contain from 1 to about 20 carbon atoms and include straight and branched alkyl radicals, cyclic hydrocarbon radicals, alkyl-substituted cyclic hydrocarbon radicals, aromatic radicals, alkyl-substituted aromatic radicals. Suitable substituted hydrocarbyl radicals are hydrocarbyl radicals as defined above which are independently substituted with one or more halogen, amido, phosphido, alkoxy, metalloid or other Lewis acidic or basic functionality, such as, trifluoromethyl, dimethylaminomethyl, diphenylphosphinomethyl, methoxymethyl, phenoxyethyl trimethylsilylmethyl and the like. Suitable organometallic radicals for R or R' in all the above formulae include trimethylsilyl, triethylsilyl, ethyldimethylsilyl, methyldiethylsilyl, triphenylgermyl and the like.

In cationic form activated for olefin polymerization, the monocyclopentadienyl transition metal complex has the formula:

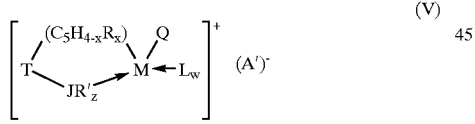
(V)

wherein M, $C_5H_{4-x}R_x$, R, x, T, J, z, R', L, w and A' are as defined above.

In an alternative embodiment, the transition metal component of the catalyst system has one of the formulae:

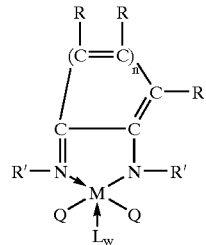
(VI)

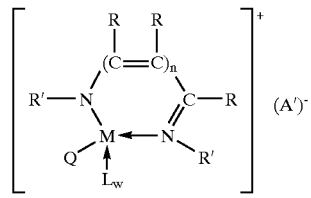
(VII)

wherein n is 1, 2, 3 or 4 and M, N, Q, L, w, R' and R are as defined above, except that R independently may also be hydrogen except for the R groups attached to the carbon atoms directly bonded to the nitrogen atoms.

In cationic forms activated for olefin polymerization the transition metal complexes of formulae (VI) and (VII) have the representative formulae:

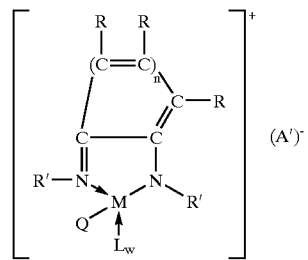
(VIII)

(IX)
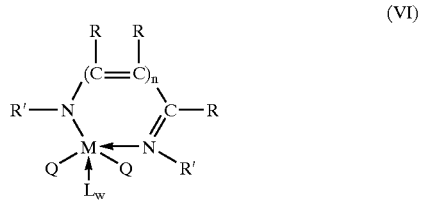

wherein M, N, R, R', Q, L, w, n and A' are as defined above.

Table 1 below depicts representative constituent moieties for the Group 3 or Lanthanide transition metal components of the present catalyst system, but the list is for illustrative purposes only and should not be construed to be limiting in any way. A number of final compounds may be formed by permuting possible combinations of the constituent moieties with each other. Some changes in nomenclature may be required. For example, if 1,2-dimethylcyclopentadienyl is bridged via the "5" position, it can become 2,3-dimethylcyclopentadienyl. When a specific isomer is not specified, all possible isomers are included. For example, when Q=propoxy, n-propoxy, and i-propoxy are included. Specific representative examples include cyclopentadienyl-dimethylsilylene-pyridyl-scandium-dihydride; methylcyclopentadienyl-phenylene-dimethylamino-yttrium-dichloride; tetramethylcyclopentadienyl-methylphenylsilylene-diphenylamino-lanthanum-diethyl; and the like.

TABLE 1

| M | Q | C₅H₄₋ₓRₓ | T | JR'z (z = 1) | —NR'=T—NR'— |
|---|---|---|---|---|---|
| Scandium | Hydride | Cyclopentadienyl | Methylene | (z = 1) | N,N'-bis(2,6-dimethylphenyl)-3-imino-1,3-dimethylpropeneanimato |
| Yttrium | Chloro | Methylcyclopentadienyl | Ethylene | methoxy | N,N'-bis(2,6-trimethylphenyl)-3-imino-1,3-dimethyl propeneanimato |
| Lanthanum | Fluoro | Ethylcyclopentadienyl | Propylene | ethoxy | N,N'-bis(2,6-diethylphenyl)-3-imino-1,3-dimethyl propeneanimato |
| Cerium | Bromo | n-propylcyclopentadienyl | Butylene | propoxy | N,N'-bis(2,6-diisopropyl-phenyl)-3-imino-1,3-dimethyl propeneanimato |
| Praseodymium | Iodo | i-propylcyclopentadienyl | 1,2-cyclohexylene | pentoxy | N,N'-bis(2-methylphenyl)-3-imino-1,3-dimethyl propeneanimato |
| Neodymium | Methyl | n-butylcyclopentadienyl | 1,2-cyclooctylene | hexoxy | N-(2-methylphenyl)-N'-(2-ethylphenyl)-3-imino-1,3-dimethyl propeneanimato |
| Samarium | Ethyl | t-butylcyclopentadienyl | 1,2-cyclododecylene | heptoxy | N-(2-methylphenyl)-N'-(2-ethylphenyl)-3-imino-1,3-dimethyl propeneanimato |
| Europium | n-propyl | (cyclohexylmethyl)cyclopentadienyl | o-phenylene | octoxy | |
| Gadolinium | isopropyl | n-hexylcyclopentadienyl | m-phenylene | phenoxy | N-(2-methylphenyl)-N'-(2-isopropylphenyl)-3-imino-1,3-dimethyl propeneanimato |
| Erbium | n-butyl | n-octylcyclopentadienyl | o-xylylene | benzyloxy | |
| Dysprosium | isobutyl | β-phenylpropylcyclopentadienyl | m-xylylene | methylthio | N,N'-bis(2,6-dimethylphenyl)-3-imino- 1,3-dimethylpropeneanimato |
| Holmium | amyl | Phenylcyclopentadienyl | Dimethylsilylene | ethylthio | |
| Erbium | isoamyl | Benzylcyclopentadienyl | Diethylsilylene | propylthio | N-phenyl-7-(phenylimino)-1,3,5-cycloheptatrien-1-ylanimato |
| Thulium | hexyl | (diphenylmethyl)cyclopentadienyl | di-n-propylsilylene | methylseleneno | |
| Ytterbium | heptyl | Trimethylgermylcyclopentadienyl | Diisopropylsilylene | phenylseleneno | N-(2,6-dimethylphenyl)-7-(2,6-dimethylphenylimino)-1,3,5-cycloheptatrien-1-ylanimato |
| Lutetium | octyl | Trimethylstannylcyclopentadienyl | di-n-butylsilylene | (z = 2) | |
| | nonyl | Triethylplumylcyclopentadienyl | di-n-hexylsilylene | dimethylamino | N-phenyl-7-(2,6-dimethylphenyl)-1,3,5-cycloheptatrien-1-ylanimato |
| | decyl | Trifluoromethylcyclopentadienyl | Methylphenylsilylene | diethylamino | |
| | cetyl | Trimethylsilylcyclopentadienyl | Diphenylsilylene | dipropylamino | N-phenyl-7-(phenylimino)-2,4,5-trimethyl-1,3,5-cycloheptatrien-1-ylanimato |
| | phenyl | 1,2-dimethylcyclopentadienyl | Dicyclohexylsilylene | dibutylamino | |
| | benzyl | 1,3-dimethylcyclopentadienyl | Tetramethyldisilylene | dipentylamino | |
| | (trimethylsilyl)methyl | 1,2-diethylcyclopentadienyl | Tetraphenyldisilylene | dicyclopentylamino | |
| | methoxy | 1,3-diethylcyclopentadienyl | Tetramethyldisiloxene | dihexylamino | |
| | ethoxy | 1,3-di-n-propylcyclopentadienyl | Pentamethyldisilazene | dicyclohexylamino | |
| | propoxy | 1,3-diphenylcyclopentadienyl | bis(1,1-methylene)dimethylsilane | methylcyclohexylamino | |
| | butoxy | 1,2-diphenylcyclopentadienyl | 1,1-bis(dimethylsilylene)-methane | methylphenylamino | |
| | phenoxy | 1-methyl-3-phenylcyclopentadienyl | 1,1,4,4-tetramethyl-disilylethylene | methyl-n-hexylamino | |
| | dimethylamido | 1-methyl-3-t-butylcyclopentadienyl | Methylazanediyl | methylphenylphosphino | |

TABLE 1-continued

| M | Q | T | E | L(optional) |
|---|---|---|---|---|
| | diethylamido | Ethylazanediyl | | |
| | methylethylamido | i-butylazanediyl | | |
| | di-t-butylamido | t-butylazanediyl | | |
| | diphenylamido | n-hexylazanediyl | | |
| | diphenylphosphido | n-octylazanediyl | | |
| | dicyclohexylphosphido | Phenylazanediyl | | |
| | Dimethylphosphido | p-n-butylphenylazanediyl | allyl | diethyl ether |
| | 1-methyl-3-isopropylcyclopentadienyl | Ethylazanediyl | dimethylphosphino | |
| | 1-methyl-3-n-butylcyclopentadienyl | i-butylazanediyl | diphenylphosphino | |
| | 1-cyclohexyl-3-methylcyclopentadienyl | t-butylazanediyl | dicyclohexylphosphino | |
| | Indenyl | n-hexylazanediyl | dimethylarsenio | |
| | 2-methylindenyl | n-octylazanediyl | diphenylarsenio | |
| | 2-methyl-4-phenylindenyl | Phenylazanediyl | | |
| | 2-methyl-4-naphylindenyl | p-n-butylphenylazanediyl | allyl | diethyl ether |
| M | $C_5H_{4-x}R_x$ | T | E | L(optional) |
| | 4-phenylindenyl | 2,5-di-t-butylphenyl-azanediyl | phenyl | Tetrahydrofuran |
| | 2-isopropylindenyl | Perfluorophenylazanediyl | benzyl | Dimethylaniline |
| | 2-isopropyl-4-phenylindenyl | Benzylazanediyl | napthyl | Trimethylphosphine |
| | 2,3-dimethylindenyl | Cyclohexylazanediyl | pyridyl | lithium chloride |
| | 2,3,4,6-tetramethylindenyl | Cyclooctylazanediyl | pyrrolyl | Ethylene |
| | 2-methylbenzindenyl | Cyclodecylazanediyl | 2H-pyrrolyl | 1-butene |
| | Tetrahydroindenyl | Cyclododecylazanediyl | imidazolyl | 2-butene |
| | 4,7-dimethylindenyl | 2-norbornylazanediyl | pyrazolyl | Trimethylamine |
| | 2,4,7-trimethylindenyl | 1-adamantylazanediyl | isothiazolyl | tri-n-butylamine |
| | Fluorenyl | Ethylphosphinediyl | isoxazolyl | tri-n-butylamine |
| | 2,7-di-t-butylfluorenyl | Phenylphosphinediyl | pyrazinyl | styrene |
| | 2,7-dimethylfluorenyl | Cyclohexylphosphinediyl | furyl | p-methylstyrene |
| | Octahydrofluorenyl | | pyranyl | propylene |
| | 2-methyl-7-t-butylfluorenyl | | tetrahydrofuryl | octene |
| | Silacyclopentadienyl | | thienyl | |
| | Germacyclopentadienyl | | pyrimidyl | |
| | Azacyclopentadienyl | | pyridazinyl | |
| | Phosphacyclopentadienyl | | pyrrolinyl | |
| | Azaindenyl | | imidazolinyl | |
| | 2,6-dimethylazapentalene | | pyrazolinyl | |
| | octahydroocotamethylfluorenyl | | silabenzene | |
| | boratabenzene | | | |
| | allyl | | | |
| | pentadienyl | | | |
| | 3,3-dimethylcyclohexadienyl | | | |
| | Methylidene | | | |
| | Ethylidene | | | |
| | Propylidene | | | |
| | 1,3-butadiene | | | |
| | 2,4-dimethyl-1,3-butadiene | | | |
| | 1,3-pentadiene | | | |
| | 1,4-pentadiene | | | |
| | 1,3-hexadiene | | | |
| | 1,4-hexadiene | | | |
| | 1,5-hexadiene | | | |
| | 2,4-hexadiene | | | |
| | 2-methyl-1,3-hexadiene | | | |
| | 2-methyl-1,3-pentadiene | | | |

Metal complexes according to the invention can be prepared by various conventional synthetic routes.

The metal compounds according to the invention are suitable for coordination polymerization when activated by methods known in the metallocene art. Suitable activators typically include alumoxane compounds, modified alumoxane compounds, and ionizing anion precursor compounds that abstract one reactive, sigma bound metal ligand thereby ionizing the metal center into a cationic complex and providing a counter-balancing weakly or noncoordinating anion, which can optionally be bound to the cationic complex so as to form a Zwitterionic catalyst.

Alkylalumoxanes and modified alkylalumoxanes are suitable as catalyst-activators, particularly for the invention metal compounds comprising halide ligands. The alumoxane component useful as a catalyst activator typically is an oligomeric aluminum compound represented by the general formula $(R^2—Al—O)_m$, which is a cyclic compound, or $R^3(R^4—Al—O)_m AlR_2$, which is a linear compound, although other structural variations may exist. In the general alumoxane formula each $R^2$-$R^5$ is independently a $C_1$ to $C_{20}$ hydrocarbyl radical, for example, methyl, ethyl, and isomers of propyl, butyl, pentyl, hexyl, heptyl, octyl, nonyl, decyl, undecyl, dodecyl, tridecyl, tetradecyl, pentadecyl, hexadecyl, heptadecyl, octadecyl, nonadecyl or icosyl, and m is an integer from 1 to about 50. Most preferably, $R^2$-$R^5$ is methyl and m is at least 4. If an alkyl aluminum halide is used in the alumoxane preparation, the $R^2$-$R^5$ can also be halide. Alumoxanes can be prepared by various procedures known in the art. For example, an aluminum alkyl may be treated with water dissolved in an inert organic solvent, or it may be contacted with a hydrated salt, such as hydrated copper sulfate suspended in an inert organic solvent, to yield an alumoxane. Generally, however prepared, the reaction of an aluminum alkyl with a limited amount of water yields a mixture of the linear and cyclic species of the alumoxane. Methylalumoxane and modified methylalumoxanes are preferred. Mixtures of different alumoxanes and modified alumoxanes may also be used. For further descriptions, see U.S. Pat. Nos. 4,665,208, 4,952,540, 5,041,584, 5,091,352, 5,206,199, 5,204,419, 4,874,734, 4,924,018, 4,908,463, 4,968,827, 5,329,032, 5,248,801, 5,235,081, 5,157,137, 5,103,031 and EP 0 561 476 A1, EP 0 279 586 B1, EP 0 516 476 A, EP 0 594 218 A1 and WO 94/10180, each being incorporated by reference for purposes of U.S. patent practice.

When the activator is an alumoxane, the preferred transition metal compound to activator molar ratio is from about 1:5000 to 1:1, more preferably from about 1:1000 to 1:10, even more preferably from about 1:500 to 1:10 and most preferably from about 1:100 to 1:10.

The term "noncoordinating anion" is recognized to mean an anion, as represented by the symbol A' above, which either does not coordinate to the metal cation or which is only weakly coordinated to it thereby remaining sufficiently labile to be displaced by a neutral Lewis base, such as an olefinically or acetylenically unsaturated monomer.

Descriptions of ionic catalysts, those comprising a transition metal cationic complex and a noncoordinating anion, suitable for coordination polymerization appear in the early work in U.S. Pat. Nos. 5,064,802, 5,132,380, 5,198,401, 5,278,119, 5,321,106, 5,347,024, 5,408,017, 5,599,671, and WO 92/00333 and WO 93/14132. These teach a preferred method of preparation wherein metallocenes are protonated by noncoordinating anion precursors such that an alkyl/hydride group is abstracted making the transition metal compound both cationic and charge-balanced by the noncoordinating anion. Since similar ligands may be present in the metal compounds of the invention, similar methods of activation to prepare active polymerization catalysts may be followed. A preferred hydrocarbyl radical Q serving as an abstractable ligand is benzyl.

Preferred noncoordinating anion precursors of this type include those of formula $[R^*_3GH][ZX^*_{4-a}R^*_a]$ where $R^*$ is independently a $C_{1-30}$ hydrocarbyl, fluorohydrocarbyl, hydrocarbylsilyl or other substituted hydrocarbyl group, G is a Group 15 element, preferably nitrogen, H is a proton capable of reacting with the Group 3 or Lanthanide metal complex, Z is a group 13 element, preferably boron or aluminum, $X^*$ is independently a substituted or unsubstituted fluorocarbyl or fluorohydrocarbyl ligand, preferably a substituted or unsubstituted aromatic fluorocarbyl or fluorohydrocarbyl ligand, and a is 0, 1 or 2. Most preferred $X^*$ radicals include perfluorophenyl, perfluoronapthyl, perfluorobiphenyl, and 3,5-bis(trifluoromethyl)phenyl. The preferred cationic portion of the noncoordinating anion precursors include [Me$_2$PhNH], [n-Bu$_3$NH], [(C$_{18}$H$_{37}$)$_2$PhNH], [(C$_{16}$H$_{33}$)$_3$NH], [(C$_{18}$H$_{37}$)$_3$NH] and the like. The preferred anionic portion of the noncoordinating anion precursors include [B(C$_6$F$_5$)$_4$], [B(C$_{10}$F$_7$)$_4$], [B(C$_{12}$F$_9$)$_4$], [MeB(C$_6$F$_5$)$_3$], [B(3,5-(CF$_3$)$_2$C$_6$H$_3$)$_4$], [B(C$_6$F$_5$)$_3$(C$_{10}$F$_7$)] and the like where C$_6$F$_5$ is perfluorophenyl, C$_{10}$F$_7$ is perfluoronapthyl and C$_{12}$F$_9$ is perfluorobiphenyl.

The use of ionizing ionic compounds not containing an active proton but capable of producing both an active metal cationic complex and a noncoordinating anion is also possible. See, EP-A-0 426 637, EP-A-0 573 403 and U.S. Pat. No. 5,387,568 for instructive ionic compounds. Reactive cations of the ionizing ionic compounds, other than the Bronsted acids, include ferrocenium, silver, tropyliurn, carbenium cations including triphenylcarbenium and silylium cations including triethylsilylium, or alkali metal or alkaline earth metal cations such as sodium, magnesium or lithium cations. A further class of noncoordinating anion precursors suitable in accordance with this invention are hydrated salts comprising the alkali metal or alkaline earth metal cations and a non-coordinating anion as described above. The hydrated salts can be prepared by reaction of the metal cation-noncoordinating anion salt with water, for example, by hydrolysis of the commercially available or readily synthesized $[Li]^+[B(Pfp)_4]^-$ which yields $[Li(H_2O)_x]^+[B(pfp)_4]^-$, where (pfp) is pentafluorophenyl or perfluorophenyl.

Any metal or metalloid capable of forming a compatible, weakly or negligibly coordinating complex may be used or contained in the noncoordinating anion. Suitable metals include, but are not limited to aluminum, gold, platinum and the like. Suitable metalloids include, but are not limited to, boron, phosphorus, silicon and the like. The description of noncoordinating anions and precursors thereto of the documents of the foregoing paragraphs are incorporated by reference for purposes of U.S. patent practice.

An additional method of making the active polymerization catalysts of this invention uses ionizing anion precursors which are initially neutral Lewis acids but form a metal cationic complex and the noncoordinating anion, or a Zwitterionic complex upon reaction with the invention compounds. For example, tris(pentafluorophenyl) boron or aluminum act to abstract a hydrocarbyl or hydride ligand to yield an invention metal cationic complex and stabilizing noncoordinating-anion, see EP-A-0 427 697 and EP-A-0 520 732 for illustration utilizing analogous Group 4 metallocene compounds. See also the methods and compounds of EP-A-0 495 375. For formation of Zwitterionic complexes using analogous Group 4 compounds see U.S. Pat. Nos. 5,624,878; 5,486,632; and 5,527,929. The description of noncoordinating anions and precursors thereto of these documents are similarly incorporated by reference for purposes of U.S. Patent practice. Lewis acid activators include those of formula $ZX^*_{3-b}R^*_b$, where Z, X* and R* are as defined above and b is 0 or 1. Preferred Lewis acid activators include $B(C_6F_5)_3$, $Al(C_6F_5)_3$, $B(C_{10}F_7)_3$, $Al(C_{10}F_7)_3$, $_{10}F_7)_3$, $B(C_{12}F_9)_3$, $Al(C_{12}F_9)_3$ and the like.

When the cation portion of an ionic noncoordinating anion precursor is a Bronsted acid such as protons or protonated Lewis bases (excluding water), or a reducible Lewis acid such as ferrocenium or silver cations, or alkaline metal or alkaline earth metal cations such as those of sodium, magnesium or lithium cations, or a neutral Lewis base such as $B(C_6F_5)_3$ or $Al(C_6F_5)_3$, the transition metal to activator molar ratio may be any ratio, but preferably from about 10:1 to 1:10, more preferably from about 5:1 to 1:5, even more preferably from about 2:1 to 1:2 and most preferably from about 1.2:1 to 1:1.2 with the ratio of about 1:1 being the most preferred. Combinations of the activator compounds described may also be used for activation. For example, tris(perfluorophenyl) boron can be used in conjunction with methylalumoxane.

The catalyst complexes of the invention are useful in polymerization of unsaturated monomers conventionally known to be polymerizable under coordination polymerization conditions using metallocenes. Such conditions are well known and include solution polymerization, slurry polymerization, gas-phase polymerization, and high pressure polymerization. The catalyst of the invention may be supported and as such will be particularly useful in the known operating modes employing fixed-bed, moving-bed, fluid-bed, slurry or solution processes conducted in single, series or parallel reactors.

When using the catalysts of the invention, particularly when immobilized on a support, the total catalyst system will generally additionally comprise one or more scavenging compounds. The term "scavenging compounds" as used in this application and its claims is meant to include those compounds effective for removing polar impurities from the reaction environment. Impurities can be inadvertently introduced with any of the polymerization reaction components, particularly with solvent, monomer and catalyst feed, and adversely affect catalyst activity and stability. It can result in decreasing or even elimination of catalytic activity, particularly when ionizing anion pre-cursors activate the catalyst system. The polar impurities, or catalyst poisons include water, oxygen, metal impurities, etc. Preferably steps are taken before provision of such into the reaction vessel, for example by chemical treatment or careful separation techniques after or during the synthesis or preparation of the various components, but some minor amounts of scavenging compound will still normally be used in the polymerization process itself.

Typically the scavenging compound will be an organometallic compound such as the Group 13 organometallic compounds of U.S. Pat. Nos. 5,153,157, 5,241,025 and WO-A-91/09882, WO-A-94/03506, WO-A-93/14132, and that of WO 95/07941. Exemplary compounds include triethyl aluminum, triethyl borane, triisobutyl aluminum, methylalumoxane, isobutyl aluminumoxane, and tri-n-octyl aluminum. Those scavenging compounds having bulky or $C_6$–$C_{20}$ linear hydrocarbyl substituents covalently bound to the metal or metalloid center are preferred to minimize adverse interaction with the active catalyst. Examples include triethylaluminum, but more preferably, bulky compounds such as triisobutylaluminum, triisoprenylaluminum, and long-chain linear alkyl-substituted aluminum compounds, such as tri-n-hexylaluminum, tri-n-octylaluminum, or tri-n-dodecylaluminum. When alumoxane is used as activator, any excess over the amount needed to activate the catalysts present will act as scavenger compounds and additional scavenging compounds may not be necessary. Alumoxanes also may be used in scavenging amounts with other means of activation, e.g., methylalumoxane, $[Me_2HNPh]^+[B(pfP)_4]$ or $B(Pfp)_3$. The amount of scavenging agent to be used with the catalyst compounds of the invention is minimized during polymerization reactions to that amount effective to enhance activity and avoided altogether if the feeds can be sufficiently free of adventitious impurities.

The catalyst according to the invention may be supported for use in gas phase, bulk, slurry polymerization processes, or otherwise as needed. Numerous methods of support are known in the art for copolymerization processes for olefins, particularly for catalysts activated by alumoxanes, any are suitable for the invention process in its broadest scope. See, for example, U.S. Pat. Nos. 5,057,475 and 5,227,440. An example of supported ionic catalysts appears in WO 94/03056. A particularly effective method is that described U.S. Pat. No. 5,643,847, and WO 96/04319. A bulk, or slurry, process utilizing supported, invention metal compounds activated with alumoxane co-catalysts can be utilized as described for ethylene-propylene rubber in U.S. Pat. Nos. 5,001,205 and 5,229,478, and these processes will additionally be suitable with the catalyst systems of this application. Both inorganic oxide and polymeric supports may be utilized in accordance with the knowledge in the field. See U.S. Pat. Nos. 5,422,325, 5,427,991, 5,498,582 and 5,466,649, and international publications WO 93/11172 and WO 94/07928. Each of the foregoing documents is incorporated by reference for purposes of U.S. patent practice.

In preferred embodiments of the process for this invention, the catalyst system is employed in liquid phase (solution, slurry, suspension, bulk phase or combinations thereof), in high pressure liquid or supercritical fluid phase, or in gas phase. Each of these processes may be employed in singular, parallel or series reactors. The liquid processes comprise contacting olefin monomers with the above described catalyst system in a suitable diluent or solvent and allowing said monomers to react for a sufficient time to produce the copolymers in accordance with the invention. Hydrocarbyl solvents are suitable, both aliphatic and aromatic, hexane and toluene are preferred. Bulk and slurry processes are typically done by contacting the catalysts with a slurry of liquid monomer, the catalyst system being supported. Gas phase processes typically use a supported catalyst and are conducted in any manner known to be suitable for ethylene homopolymers or copolymers prepared by coordination polymerization. Illustrative examples may be found in U.S. Pat. Nos. 4,543,399, 4,588,790, 5,028,670, 5,382,638, 5352,749, 5,436,304, 5,453,471, and 5,463,999, and WO 95/07942. Each is incorporated by reference for purposes of U.S. patent practice.

Generally speaking the polymerization reaction temperature can vary from about −50° C. to about 250° C. Preferably the reaction temperature conditions will be from −20° C. to 220°, more preferably below 200° C. The pressure can vary from about 1 mm Hg to 2500 bar, preferably from 0.1 bar to 1600 bar, most preferably from 1.0 to 500 bar.

Linear polyethylene, including high and ultra-high molecular weight polyethylenes, including both homo- and copolymers with other alpha-olefin monomers, alpha-olefinic and/or non-conjugated diolefins, for example, $C_3$–$C_{20}$ olefins, $C_4$–$C_{20}$ diolefins, $C_4$–$C_{20}$ cyclic olefins or $C_8$–$C_{20}$ styrenic olefins, are produced by adding ethylene, and optionally one or more of the other monomers, to a reaction vessel at a typical temperature of 20–250° C. with the invention catalyst that has been slurried with or dissolved in a solvent, such as hexane or toluene. Heat of polymerization is typically removed by cooling. Gas phase polymerization can be conducted, for example, in a continuous fluid bed gas-phase reactor operated at about 200–3000 kPa and 60–160° C., using hydrogen as a reaction modifier (100–200 ppm), $C_4$–$C_8$, comonomer feedstream (0.5–12 mol %), and $C_2$ feedstream (25–35 mol %). See, U.S. Pat. Nos. 4,543, 399, 4,588,790, 5,028,670 and 5,405,922 and 5,462,999, which are incorporated by reference for purposes of U.S. patent practice.

Ethylene-α-olefin (including ethylene-cyclic olefin and ethylene-α-olefin-diolefin) elastomers of high molecular weight and low crystallinity can be prepared utilizing the catalysts of the invention under traditional solution polymerization processes or by introducing ethylene gas into a slurry utilizing the α-olefin or cyclic olefin or mixtures thereof with other monomers, polymerizable and not, as a polymerization diluent in which the invention catalyst is suspended. Typical ethylene pressures will be between 10 and 1000 psig (69–6895 kPa) and the polymerization diluent temperature will typically be between –10–160° C. The process can be carried out in a stirred tank reactor, or more than one reactor operated in series or parallel. See the general disclosure of U.S. Pat. No. 5,001,205 which is incorporated by reference for its description of polymerization processes, ionic activators and useful scavenging compounds.

Pre-polymerization of the supported catalyst of the invention may also be used for further control of polymer particle morphology in typical slurry or gas phase reaction processes in accordance with conventional teachings. For example, such can be accomplished by pre-polymerizing ethylene or a $C_3$–$C_6$ α-olefin for a limited time, for example, ethylene is contacted with the supported catalyst at a temperature of –15° to 30° C. and ethylene pressure of up to about 250 psig (1724 kPa) for 75 min to obtain a polymeric coating on the support of polyethylene of 30,000–150,000 molecular weight. The pre-polymerized catalyst is then available for use in the polymerization processes referred to above. The use of polymeric resins as a support coating may additionally be utilized, typically by suspending a solid support in dissolved resin of such material as polystyrene with subsequent separation and drying.

Other olefinically unsaturated monomers besides those specifically described above may be polymerized using the catalysts according to the invention, for example, styrene, alkyl-substituted styrene, ethylidene norbomene, norbomadiene, dicyclopentadiene, vinylcyclohexane, vinylcyclohexene and other olefinically-unsaturated monomers, including other cyclic olefins, such as cyclopentene, norbornene, and alkyl-substituted norbornenes. Additionally, α-olefinic macromonomers of up to 1000 mer units, or more, may also be incorporated by copolymerization.

The catalyst compositions of the invention can be used as described above individually for coordination polymerization or can be mixed to prepare polymer blends with other known olefin polymerization catalyst compounds. By selection of monomers, blends of coordination catalyst compounds, polymer blends can be prepared under polymerization conditions analogous to those using individual catalyst compositions. Polymers having increased MWD for improved processing and other traditional benefits available from polymers made with mixed catalyst systems can thus be achieved.

EXAMPLES

The following examples are presented to illustrate the foregoing discussion. All parts, proportions, and percentages are by weight unless otherwise indicated. All reactions and manipulations have been conducted using dry, oxygen-free solvents under an inert nitrogen or argon atmosphere. Although the examples may be directed toward certain embodiments of the present invention, they are not to be viewed as limiting the invention in any specific respect. In these examples, certain abbreviations are used to facilitate the description. These include standard chemical abbreviations for the elements and certain commonly accepted abbreviations, such as: Me=methyl, Et=ethyl, Bu=butyl, Ph=phenyl, MAO=methylalumoxane, and THF=tetrahydrofuran.

All molecular weights are weight average molecular weight unless otherwise noted. Molecular weights (weight average molecular weight (Mw) and number average molecular weight (Mn)) were measured by Gel Permeation Chromatography, unless otherwise noted, using a Waters 150 Gel Permeation Chromatograph equipped with a differential refractive index detector and calibrated using polystyrene standards. Samples were run in either THF (45° C.) or in 1,2,4-trichlorobenzene (145° C.) depending upon the sample's solubility using three Shodex GPC AT-80 M/S columns in series. This general technique is discussed in "Liquid Chromatography of Polymers and Related Materials III" J. Cazes Ed., Marcel Decker, 1981, page 207, which is incorporated by reference for purposes of U.S. patent practice herein. No corrections for column spreading were employed; however, data on generally accepted standards, e.g. National Bureau of Standards Polyethylene 1475, demonstrated a precision with 0.1 units for Mw/Mn which was calculated from elution times. The numerical analyses were performed using Expert Ease® software available from Waters Corporation. The term "psid" refers to the differential pressure resulting from the addition of monomer.

Example 1

Synthesis of (dimethylaminoethyl) tetramethylcyclopentadienyl-scandiumdichloride, $(CH_2)_2(C_5Me_4)(NMe_2)ScCl_2$ (1)

To a solution of Li metal (10.2 g, 1.47 mol) in $Et_2O$ (300 ml) 2-bromo-2-butene (100 g, 0.74 mol) was added over 2 hours under and argon flow at a rate sufficient to maintain a reflux. The reaction was stirred for 4 hours at ambient temperature and then ethyl-3-(N,N-dimethylamino) propionate (50 g, 0.35 mole) was added over 1.5 hours maintaining a reflux. The reaction was stirred for 15 hours at ambient temperature. The reaction was poured into aqueous $NH_4Cl$ (200 ml) and stirred until all of the Li was deactivated. The phases were separated and the aqueous phase was extracted with $Et_2O$ (4×100 ml). The combined organics were dried over $MgSO_4$, filtered and the solvent was removed under reduced pressure yielding an orange oil (50 g, 67 mol %).

The oil in $Et_2O$ was added to a solution of p-toluenesulfonic acid-$H_2O$ (47 g, 0.23 mol) in $Et_2O$. The reaction was stirred for 3 hours. The reaction was poured into aqueous $Na_2CO_3$. The phases were separated and the aqueous phase was extracted with $Et_2O$ (3×50 ml). The combined organics were dried over $MgSO_4$, filtered, and the solvent was removed under reduced pressure yielding an orange oil. The oil was distilled at reduced pressure (35–40° C./0.010 torr) yielding a yellow oil (24.1 g, 55 mol %).

In a drybox n-BuLi (10.3 ml, 0.026 mol) was added to a solution of the compound prepared above (5.0 g, 0.026 mol) in pentane (150 ml) and the reaction stirred overnight. The solution was filtered, washed with pentane, and the solid dried.

The above solid (2.17 g, 0.011 mol) was dissolved in THF and $ScCl_3$ (1.65 g, 0.011 mol) was added over several minutes. The reaction was stirred for 18 hours, filtered, and the THF removed under reduced pressure yielding a red oil. Petroleum ether was added to the oil and the resulting solution filtered to yield an orange solid (3.1 g, 92 mol %).

Example 2

Synthesis of (dimethylaminoethyl) tetramethylcyclopentadienyl-scandiumdibenzyl, $(CH_2)_2(C_5Me_4)(NMe_2)Sc(CH_2C_6H_5)_2$ (2)

In a drybox $(CH_2)_2(C_5Me_4)(NMe_2)ScCl_2$ (1.33 g, 0.00431 mol) was slurried in toluene. To this solution benzyl Grignard (2.0 M in THF, 6 ml) was added over 20 minutes. The reaction was stirred for 16 hours, filtered, and the solid washed with toluene. The solvent was removed under reduced pressure. Toluene was added to the solid, the solution was filtered and the toluene removed under reduced pressure, and the resulting yellow-orange solid dried (1.6 g, 89 mol %). The solid was recrystallized from toluene to give pale yellow crystals. The structure of this compound was confirmed by a single crystal x-ray analysis.

Example 3

Formation of $[(CH_2)_2(C_5Me_4)(NMe_2C_6H_5)]^+$ $[(C_6H_5CH_2)B^-(C_6F_5)_3]^-$ and Polymerization of Ethylene (3)

In the drybox $(CH_2)_2(C_5Me_4)(NMe_2)Sc(CH_2C_6H_5)_2$ (12 mg, 0.0286 mmol) was loaded into an NMR tube and dissolved in toluene-$d_8$. To this solution, $B(C_6F_5)_3$ (15 mg, 0.029 mmol) was added and the solution turned yellow. Within several minutes a yellow oil had separated out. Ethylene (10 ml, 99.99+%) was added to the tube through a cap via a gas tight syringe. Within several minutes polymer was noticeable on the walls of the tube.

Example 4

Ethylene Polymerization with $(CH_2)_2(C_5Me_4)(NMe_2)ScCl_2$ (4)

Polymerization runs were carried out in a 1 L reactor using the catalyst system prepared by activation of $(CH_2)_2(C_5Me_4)(NMe_2)ScCl_2$ with methylalumoxane. The catalyst was prepared with an aluminum to scandium molar ratio of 925/1. The polymerizations were carried out in 400 ml of toluene at 80° C. for 15 minutes under 65 psid (4.5 bars) continuous ethylene pressure. The catalyst produced 2.8 g of polyethylene with an activity of 781 kgPE/molSc·atm·h. The product obtained had Mw of 370,000 and MWD of 2.11 indicative of single site catalyst behavior.

Example 5

Ethylene/Hexene Polymerization with $(CH_2)_2(C_5Me_4)(NMe_2)ScCl_2$ (5)

Polymerization runs were carried out in a 1 L reactor using the catalyst system prepared by activation of $(CH_2)_2(C_5Me_4)(NMe_2)ScCl_2$ with methylalumoxane. The catalyst was prepared with an aluminum to scandium molar ratio of between 460–500/1. The polymerizations were carried out in 350 ml of toluene at 60° C. for 15 minutes with 50 ml of 1-hexene and 65 psid (4.5 bars) continuous ethylene pressure. The catalyst produced 1.0 g of ethylene-1-hexene copolymer with an activity of 93 kg polymer/mol Sc·atm·h. The product obtained had an Mw of 441,000 and an MWD of 2.70 indicative of single site catalyst behavior. $^1$H NMR of the polymer indicated 3.5 mol % 1-hexene incorporated into the polymer.

Example 6

Ethylene Polymerization with $(CH_2)_2(C_5Me_4)(NMe_2)Sc(CH_2C_6H_5)_2$ and N,N-Dimethyanilinium tetrakis-perfluorophenyl boron $[DAMH]^+[B(pfp)_4]^-$ (6)

Polymerization runs were carried out using the catalyst system prepared by activation of $(CH_2)_2(C_5Me_4)(NMe_2)Sc(CH_2C_6H_5)_2$ with $[DMAH]^+[B(pfp)_4]^-$. $(CH_2)_2(C_5Me_4)(NMe_2)Sc(CH_2C_6H_5)_2$ (20 mg) was weighed out under inert atmosphere conditions and $[DMAH]^+[B(PfP)_4]^-$ activator was added in a 1/1 molar ratio. Dry toluene (2 ml) was added via pipette and the mixture was allowed to stand (10–15 minutes) with occasional stirring to allow for complete activation.

To a dry $N_2$-purged, 1 liter autoclave reactor dry toluene (0.4 L) was added. While the solvent was stirred under $N_2$-purge, triethylaluminum (25 wt % TEAL in heptane, 0.2 ml) was added as a scavenger to the reactor via syringe through a purge port using standard air sensitive technique. The reactor was then equilibrated to 80° C. The pre-activated catalyst was then added to the reactor through a port using air sensitive technique. The reactor was then pressurized with 65 psid (4.5 bars) ethylene with a replenishing flow. The mixture was then stirred at 80° C. for 15 minutes.

The polymer obtained was dried in a vacuum oven. The resulting polymer, 1.3 g, had Mw=7000 and MWD=1.93 indicative of single site catalyst behavior. (catalyst activity= 25 kg polymer/molSc·atm·h).

Example 7

Ethylene Polymerization with $(CH_2)_2(C_5Me_4)(NMe_2)Sc(CH_2C_6H_5)_2$ and N,N-Dimethyanilinium tetrakis-perfluorophenyl boron, $[DMAH]^+[B(pfp)_4]^-$ (7)

Polymerization runs were carried out using the catalyst system prepared by activation of $(CH_2)_2(C_5Me_4)(NMe_2)Sc(CH_2C_6H_5)_2$ with $[DMAH]^+[B(pfp)_4]^-$. $(CH_2)_2(C_5Me_4)(NMe_2)Sc(CH_2C_6H_5)_2$ (10 mg) was weighed out under inert atmosphere conditions and $[DMAH]^+[B(Pfp)_4]^-$ activator was added with a 1/1 molar ratio. Dry toluene (2 ml) was added via pipette and the mixture was allowed to stand (10–15 minutes) with occasional stirring to allow for complete activation.

To a dry $N_2$-purged, 1 liter autoclave reactor dry toluene (0.4 L) was added. While the solvent was stirred under $N_2$-purge, triethylaluminum (25 wt % TEAL in heptane, 0.2 ml) was added as a scavenger to the reactor via syringe through a purge port using standard air sensitive technique. The reactor was then equilibrated to 80° C. The pre-activated catalyst was then added to the reactor through a port using air sensitive technique. The reactor was then pressurized with 65 psid (4.5 bars) ethylene with a replenishing flow. The mixture was then stirred at 80° C. for 15 minutes.

The polymer obtained was dried in a vacuum oven. The resulting polymer, 0.9 g, had Mw=171,000 and bimodal MWD=10.96. (Catalyst activity=34 kg polymer/mol Sc·atm·h).

Example 8

Synthesis of N,N'-bis-(2,6-diisopropylphenyl)-3-iminopropeneaminato-scandium Dichloride The hydrochloride salt of N,N'-bis-(2,6-diisopropylphenyl)-3-iminopropeneamine (0.487 g, 1.14 mmol) was suspended into 15 ml of anhydrous THF at −80° C. n-Butyl lithium (2.1 ml) was added dropwise to the stirred suspension. Upon complete addition, the solution was stirred and allowed to warm to room temperature over 50 minutes. The solution was then cooled to −80° C. whereupon 0.17 g (1.12 mmol) of anhydrous scandium trichloride was added. The reaction was stirred and allowed to warm to room temperature over one hour. The THF was then removed in vacuo. The residue was dissolved into hexane and filtered. The solution was dried in vacuo to remove solvent. The residue was dissolved into pentane forming two phases. The lighter pentane rich phase was separated and pentane removed until crystallization ensued. The crystalline solid was dried in vacuo. A $^1$H-NMR was recorded in benzene. The spectrum clearly shows 1 equivalent of coordinated THF. The chemical shifts are as follows: 11.6 ppm, broad singlet (bs), 1H beta to NAr; 7.12 ppm, 6H, Ar—$\underline{H}$; 4.80 ppm, t, 2H alpha to NAr; 3.60 ppm, m, 4H alpha to O in THF; 3.30 ppm, h, 4H, $\underline{H}$—C(CH$_3$)$_2$; 1.35 ppm, m, 4H beta to O in THF; 1.19 ppm, d, 12H, C$\underline{H}_3$.

Example 9

Synthesis of N,N'-bis-(2,6-dimethylphenyl)-3-imino-1,3-dimethyl-propeneaminato-scandium Dichloride The lithium salt of N,N'-bis-(2,6-dimethylphenyl)-3-imino-1,3-dimethyl-propeneamine (1.02 g, 3.3 mmol) was dissolved into 11 ml of anhydrous THF and cooled to −20° C. Separately, scandium trichloride (0.45 g, 3.0 mmol) was suspended into 11 ml of anhydrous THF and cooled to −20° C. The ligand solution was then added dropwise to the scandium suspension. Upon complete addition, the mixture was stirred and slowly warmed to room temperature. The reaction was continued overnight. THF was then removed in vacuo. The residue was extracted with toluene and filtered. The solution was concentrated, hexane added and the solution cooled to −80° C. where the product crystallized as yellow microcrystals. The product was collected by filtration and washed with pentane. The crystals were dried in vacuo. Isolated yield: 550 mg (44 mol %).

Example 10

Ethylene Polymerization with N,N'-bis-(2,6-dimethylphenyl)-3-imino-1,3-dimethyl-propeneaminato-scandium Dichloride and MAO To a 300 ml Parr reactor 203 milligrams of solid methylaluminoxane was dissolved into 50 ml of toluene. Separately, 29 milligrams of the compound from Example 9 was dissolved into approximately 1.5 ml of toluene. This compound was activated by the addition of approximately 1.5 ml of a toluene solution containing 203 milligrams of MAO. The prepared catalyst had an aluminum to scandium molar ratio of 50:1. This activated catalyst mixture was added to the reactor. The reactor was sealed and warmed to 40° C. The reactor was then charged with 40 psid (2.76 bars) of ethylene with a replenishing flow. Polymerization was continued for 30 minutes. The temperature was controlled to between 39 and 45° C. The reactor was depressurized and 100 ml of 2 N aqueous hydrochloric acid was added. Polymer, 0.2 g, was collected by filtering the resulting two phase solution. The catalyst had an activity of 1.6 kg PE/mol Sc·atm·hr. The polymer obtained had an $M_w$ of 41,900 and an MWD of 3.6.

Example 11

Ethylene Polymerization with N,N'-bis-(2,6-dimethylphenyl)-3-imino-1,3-dimethyl-propeneaminato-scandium Dichloride and MAO To a 300 ml Parr reactor 203 milligrams of solid methylaluminoxane was dissolved into 50 ml of toluene. Separately, 29 milligrams of the compound from Example 9 was dissolved into approximately 1.5 ml of toluene. This compound was activated by the addition of approximately 1.5 ml of a toluene solution containing 203 milligrams of MAO. The prepared catalyst had an aluminum to scandium molar ratio of 50:1. This activated catalyst mixture was added to the reactor. The reactor was sealed and warmed to 50° C. The reactor was then charged with 40 psid (2.76 bars) of ethylene with a replenishing flow. Polymerization was continued for 30 minutes. The temperature was controlled to between 47 and 56° C. The reactor was depressurized and 100 ml of 2 N aqueous hydrochloric acid was added. Polymer, 0.16 g, was collected by filtering the resulting two phase solution. The catalyst had an activity of 1.2 kg PE/mol Sc·atm·hr. The polymer obtained had an $M_w$ of 42,100 and an MWD of 3.7.

Example 12

Comparative Example with N,N'-bis-(2,6-diisopropylphenyl)-3-iminopropeneaminat-scandium Dichloride and MAO To a 300 ml Parr reactor 203 milligrams of solid methylaluminoxane was dissolved into 50 ml of toluene. Separately, 40 milligrams of the compound from Example 8 was dissolved into approximately 1.5 ml of toluene. This compound was combined with MAO by the addition of approximately 1.5 ml of a toluene solution containing 203 milligrams of the MAO. The prepared catalyst had an aluminum to scandium molar ratio of 50:1. The reagent mixture/reaction product was colorless. It was added as such to the reactor. The reactor was sealed and warmed to 40° C. The reactor was then charged with 40 psid (2.76 bars) of ethylene with a replenishing flow. The contacting of ethylene with the reagent mixture/reaction product was continued for 30 minutes. The temperature was controlled to between 37 and 43° C. The reactor was depressurized and 100 ml of 2 N aqueous hydrochloric acid was added. No heat of reaction nor polymer product was observed. This is believed to be due to the use of hydrogen as R groups on the carbon atoms directly bonded to the ketimato nitrogens of the metallocyclic ring. The strong Lewis acidity of the MAO likely deactivated the Scandium compound through inadvertent byproduct reactions.

While the present invention has been described and illustrated by reference to particular embodiments, it will be appreciated by those of ordinary skill in the art that the invention lends itself to many different variations not illustrated herein. For these reasons, then, reference should be made solely to the appended claims for purposes of determining the true scope of the present invention.

We claim:

1. A process for olefin polymerization comprising contacting, under olefin polymerization conditions, one or more olefin monomers with an activated Group-3 or Lanthanide metal stabilized by
   a) a monoanionic bidentate ligand, and
   b) two monoanionic ligands,
   wherein the bidentate ligand and the metal form a metallocyclic ring comprising at least five atoms.

2. The process for olefin polymerization of claim 1 wherein the metal comprises scandium or yttrium.

3. The process for olefin polymerization of claim 1 wherein the bidentate ligand has the formula:

$$(C_5H_{4-x}R_x)TE \text{ wherein}$$

a) x is a number from 0 to 4,
b) each R is, independently, a radical selected from
   (i) $C_1-C_{20}$ hydrocarbyl radicals,
   (ii) $C_1-C_{20}$ substituted hydrocarbyl radicals wherein one or more hydrogen atoms are replaced by a halogen atom, amido, phosphido, alkoxy or aryloxy or other Lewis-acid- or -base-containing radical,
   (iii) $C_1-C_{20}$ hydrocarbyl-substituted Group-14 metalloid radicals,
   (iv) halogen radicals, or
   (v) two adjacent R-groups are joined to form a $C_4-C_{20}$ ring to give a saturated or unsaturated polycyclic cyclopentadienyl ligand
c) T is a covalent bridging group containing a Group-14 or -15 element;
d) E is a π-donating ligand or $JR'_z$ wherein
   (vi) J is an element from Group-15 or -16;
   (vii) z is 2 when J is a Group-15 element and 1 when J is a Group-16 element;
   (viii) each R' is independently a radical selected from
      1) $C_1-C_{20}$ hydrocarbyl radicals,
      2) a substituted $C_1-C_{20}$ hydrocarbyl radical wherein one or more hydrogen atoms is replaced by a halogen atom, amido, phosphido, alkoxy or aryloxy or other Lewis-acid- or -base-containing radical or
      3) $C_1-C_{20}$ hydrocarbyl-substituted, Group-14 metalloid radicals.

4. The process for olefin polymerization of claim 1 wherein the ancillary ligand has the formula:

$$-NR'=T'-NR'-$$

wherein
a) N is nitrogen,
b) each R' is independently a radical selected from the group consisting of $C_1-C_{20}$ hydrocarbyl radicals, substituted $C_1-C_{20}$ hydrocarbyl radicals wherein one or more hydrogen atoms are replaced by a halogen atom, and $C_1-C_{20}$ hydrocarbyl-substituted metalloid radicals wherein the metalloid is selected from Group 14 of the Periodic Table of the Elements
c) T' is a covalent bridging group selected from $$=C(R)[C(R)=C(R)]_n-$$

and

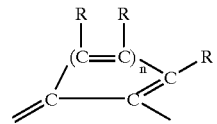

wherein each R is, independently, a radical selected from
(i) $C_1-C_{20}$ hydrocarbyl radicals,
(ii) $C_1-C_{20}$ substituted hydrocarbyl radical wherein one or more hydrogen atoms is replaced by a halogen atom, amido, phosphido, alkoxi or aryloxy or other Lewis-acid- or -base-containing radical,
(iii) $C_1-C_{20}$ hydrocarbyl-substituted Group-14 metalloid radicals,
(iv) halogen radicals, or
(v) two adjacent R groups joined to form a $C_4-C_{20}$ ring;
(vi) R independently may also be hydrogen except for R groups attached to the carbon atoms directly bonded to the nitrogen atoms, and
(vii) n is 1, 2, 3, or 4.

5. A process for olefin polymerization comprising:
a) activating a metal complex to a cationic form, wherein the metal complex comprises a Group-3 or Lanthanide metal complex of the formula

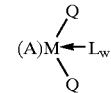

wherein,
(i) M is a Group-3 or Lanthanide metal;
(ii) A is a monoanionic bidentate ancillary ligand which forms a metallocycle with at least 5 primary atoms;
(iii) each Q is independently a monoanionic ligand;
(iv) L is a neutral Lewis base; and
(v) w is a number from 0 to 3; and p1 b) contacting one or more olefin monomers with the activated metal complex under olefin polymerization conditions.

6. The process for olefin polymerization of claim 5, wherein the Group-3 or Lanthanide metal complex has the formula

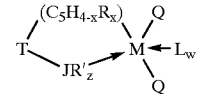

wherein
a) M is a Group-3 or Lanthanide metal;
b) $C_5H_{4-x}R_x$ is a cyclopentadienyl ring covalently π-bound to M and substituted with from zero to four substituent groups R;
c) x is a number from 0 to 4 denoting the degree of substitution of $C_5H_{4-x}R_x$;
d) each R is, independently, a radical selected from $C_1-C_{20}$ hydrocarbyl radicals, $C_1-C_{20}$ substituted hydrocarbyl radicals wherein one or more hydrogen atoms are replaced by a halogen atom, amido, phosphido, alkoxy or aryloxy or other Lewis-acid- or -base-containing radical, $C_1-C_{20}$ hydrocarbyl-substituted metalloid radicals wherein the metalloid is selected from Group-14 elements, and halogen radicals, or $C_5H_{4-x}R_x$ is a cyclopentadienyl ring in which two adjacent R-groups are joined to form a $C_4$–$C_{20}$ ring to give a saturated or unsaturated polycyclic cyclopentadienyl ligand which may be additionally substituted with one or more R groups;

e) T is a covalent bridging group containing a Group-14 or -15 element;

f) J is a Group-15 or -16 element;

g) z is 2 when J is a Group-15 element and 1 when J is a Group-16 element;

h) each R' is independently a radical selected from $C_1$–$C_{20}$ hydrocarbyl radicals, substituted $C_1$–$C_{20}$ hydrocarbyl radicals wherein one or more hydrogen atoms is replaced by a halogen atom, and $C_1$–$C_{20}$ hydrocarbyl-substituted metalloid radical wherein the metalloid is selected from Group-14 elements;

i) each Q is independently a univalent anionic ligand;

j) L is a neutral Lewis base; and k) w is a number from 0 to 3.

7. The process for olefin polymerization of claim 6 wherein M is scandium, yttrium or lanthanum.

8. The process for olefin polymerization of claim 6 wherein T is a dialkyl, alkylaryl or diaryl silicon or germanium radical.

9. The process for olefin polymerization of claim 6 wherein T is alkyl or aryl phosphine or amine radical or a hydrocarbyl radical.

10. The process for oletin polymerization of claim 6 wherein J is oxygen, sulfur, nitrogen or phosphorus.

11. The process for olefin polymerization of claim 6 wherein J is nitrogen.

12. A process for olefin polymerization comprising a) activating a Group-3 or Lanthanide metal complex to a cationic form wherein the metal complex has one of the formulas:

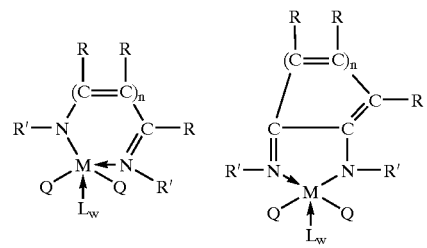

wherein (i) M is a Group-3 or Lanthanide metal;

(ii) each R' is independently a radical selected from the group consisting of $C_1$–$C_{20}$ hydrocarbyl radicals, substituted $C_1$–$C_{20}$ hydrocarbyl radicals wherein one or more hydrogen atoms are replaced by a halogen atom, and $C_1$–$C_{20}$ hydrocarbyl-substituted metalloid radicals wherein the metalloid is selected from Group 14 of the Periodic Table of the Elements iii) each R is independently hydrogen, halogen, a $C_1$–$C_{20}$ hydrocarbyl, or a substituted $C_1$–$C_{20}$ hydrocarbyl wherein one or more hydrogen atoms is replaced by a halogen atom, amido, phosphido, alkoxy or aryloxy or other Lewis-acid- or -base-containing radical, $C_1$–$C_{20}$ hydrocarbyl-substituted metalloid radical wherein the metalloid is selected from Group-14 elements, or two adjacent R-groups are joined to form a $C_4$–$C_{20}$ ring, except that R independently may also be hydrogen except for R groups attached to the carbon atoms directly bonded to the nitrogen atoms;

(iv) n is 1, 2, 3, or 4;

(v) each Q is independently a monoanionic ligand;

(vi) L is a neutral Lewis base; and (vii) w is a number from 0 to 3; and b) contacting one or more olefin monomers with the activated metal complex under olefin polymerization conditions.

13. The complex of claim 12 wherein M is scandium, yttrium, or lanthanum.

* * * * *